(12) United States Patent
Vegar et al.

(10) Patent No.: US 12,178,608 B2
(45) Date of Patent: Dec. 31, 2024

(54) INSTRUMENTED MOUTHGUARD DEVICES AND COMPONENTS CONFIGURED FOR USE IN INSTRUMENTED MOUTHGUARD DEVICES

(71) Applicant: HitIQ Limited, South Melbourne (AU)

(72) Inventors: Michael Vegar, Queenscliff (AU); Ben Nizette, Queenscliff (AU); Lucas Lang, Queenscliff (AU); David Austin, Queenscliff (AU)

(73) Assignee: HitIQ Limited, South Melbourne (AU)

( * ) Notice: Subject to any disclaimer, the term of this patent is extended or adjusted under 35 U.S.C. 154(b) by 577 days.

(21) Appl. No.: 17/427,869

(22) PCT Filed: Feb. 5, 2020

(86) PCT No.: PCT/AU2020/050096
§ 371 (c)(1),
(2) Date: Aug. 2, 2021

(87) PCT Pub. No.: WO2020/160621
PCT Pub. Date: Aug. 13, 2020

(65) Prior Publication Data
US 2022/0104768 A1    Apr. 7, 2022

(30) Foreign Application Priority Data
Feb. 6, 2019    (AU) ................. 2019900364

(51) Int. Cl.
*A61B 5/00* (2006.01)
*A61B 5/11* (2006.01)
*A63B 71/08* (2006.01)

(52) U.S. Cl.
CPC ............ *A61B 5/682* (2013.01); *A61B 5/0004* (2013.01); *A61B 5/1114* (2013.01);
(Continued)

(58) Field of Classification Search
CPC ..... A61B 5/682; A61B 5/1114; A61B 5/4064; A61B 2562/0219; A61B 2562/12; A61B 2562/164; A61B 2562/166; A63B 71/085
See application file for complete search history.

(56) References Cited

U.S. PATENT DOCUMENTS 5,718,575 A * 2/1998 Cross, III ............. A63B 71/085
433/6
8,466,794 B2    6/2013 Mack et al.
(Continued)

FOREIGN PATENT DOCUMENTS

AU    2012219306 B2    2/2011
AU    2011278996 B2    1/2012
(Continued)

OTHER PUBLICATIONS

European Search Report and Search Opinion Received for EP Application No. 20752401.8, dated on Oct. 14, 2022, 11 pages.
(Continued)

*Primary Examiner* — Eric F Winakur
*Assistant Examiner* — Abel Seifu Abegaz
(74) *Attorney, Agent, or Firm* — TraskBritt

(57) ABSTRACT

Instrumented mouthguards include components such as accelerometer modules that enable monitoring of head movements of a mouthguard wearer. Various embodiments that provide instrumented mouthguard devices and components configured for use in instrumented mouthguard devices, including flexible circuit board substrates. In some embodiments, the flexible circuit board substrate is configured to allow sizing irregularities resultant from customization of the mouthguard body to a specific wearer.

26 Claims, 7 Drawing Sheets

(52) U.S. Cl.
CPC .......... *A61B 5/4064* (2013.01); *A63B 71/085* (2013.01); *A61B 2562/0219* (2013.01); *A61B 2562/12* (2013.01); *A61B 2562/164* (2013.01); *A61B 2562/166* (2013.01)

(56) References Cited

U.S. PATENT DOCUMENTS

| | | |
|---|---|---|
| 8,537,017 B2 | 9/2013 | Mack et al. |
| 8,554,495 B2 | 10/2013 | Mack et al. |
| 9,044,198 B2 | 6/2015 | Benzel et al. |
| 9,149,227 B2 | 10/2015 | Benzel et al. |
| 9,289,176 B2 | 3/2016 | Benzel et al. |
| 9,526,289 B2 | 12/2016 | Mack et al. |
| 9,554,607 B2 | 1/2017 | Mack et al. |
| 9,585,619 B2 | 3/2017 | Benzel et al. |
| 10,420,507 B2 | 9/2019 | Calcano et al. |
| 11,678,822 B2 * | 6/2023 | Dove .................. A61B 5/1455 600/323 |
| 2014/0187875 A1 | 7/2014 | Paris et al. |
| 2014/0188010 A1 | 7/2014 | Paris et al. |
| 2015/0305671 A1 | 10/2015 | Yoon et al. |
| 2017/0156635 A1 | 6/2017 | Kuo et al. |
| 2017/0238850 A1 | 8/2017 | Gonzales et al. |
| 2018/0035952 A1 | 2/2018 | Fraylick |
| 2018/0256093 A1 | 9/2018 | Robin et al. |
| 2020/0147473 A1 * | 5/2020 | Maloney .................. A61C 7/08 |

FOREIGN PATENT DOCUMENTS

| | | |
|---|---|---|
| AU | 2011278997 B2 | 1/2012 |
| AU | 2011278999 B2 | 1/2012 |
| CA | 2805250 | 1/2012 |
| CA | 2805252 | 5/2017 |
| CA | 2837239 | 12/2017 |
| EP | 2593010 | 5/2013 |
| EP | 2675356 | 9/2016 |
| EP | 2593015 | 3/2018 |
| EP | 3329844 | 6/2018 |
| EP | 3330971 | 6/2018 |
| WO | 2019/023373 A1 | 1/2019 |

OTHER PUBLICATIONS

International Search Report for International Application No. PCT/AU2020/050096 dated May 7, 2020, 5 pages.

International Written Opinion for International Application No. PCT/AU2020/050096 dated May 7, 2020, 5 pages.

* cited by examiner

INSTRUMENTED MOUTHGUARD DEVICES AND COMPONENTS CONFIGURED FOR USE IN INSTRUMENTED MOUTHGUARD DEVICES

CROSS-REFERENCE TO RELATED APPLICATIONS

This application is a national phase entry under 35 U.S.C. § 371 of International Patent Application PCT/AU2020/050096, filed Feb. 5, 2020, designating the United States of America and published as International Patent Publication WO 2020/160621 A1 on Aug. 13, 2020, which claims the benefit under Article 8 of the Patent Cooperation Treaty to Australian Patent Application Serial No. 2019900364, filed Feb. 6, 2019.

TECHNICAL FIELD

The present disclosure relates, in various embodiments, to instrumented mouthguard devices and components configured for use in instrumented mouthguard devices. For example, this includes instrumented mouthguards that include components such as accelerometer modules that enable monitoring of head movements of a mouthguard wearer. While some embodiments will be described herein with particular reference to those applications, it will be appreciated that the present disclosure is not limited to such a field of use, and is applicable in broader contexts.

BACKGROUND

Any discussion of the background art throughout the specification should in no way be considered as an admission that such art is widely known or forms part of common general knowledge in the field.

In recent years, there has been an increasing focus on the effects of concussions and other traumatic brain injuries on participants in contact sports, such as football/rugby disciplines, martial arts, and the like. In response, various parties have explored the possibility of embedding instrumentation into mouthguards, including the likes of accelerometers and gyroscopes, thereby to collect data representative of head movements. However, as these instrumented mouthguards transition from research instruments to broader usage (for example, as consumer devices), there are challenges to be addressed in the context of device/component design and configuration.

BRIEF SUMMARY

It is an object of the present disclosure to overcome or ameliorate at least one of the disadvantages of the prior art, or to provide a useful alternative.

One embodiment provides an instrumented mouthguard device including:
a mouthguard body that is configured to be worn in a user's mouth;
a flexible circuit board substrate mounted to the mouthguard body, wherein the flexible circuit board substrate includes:
at least a first and second component zone, wherein the first and second component zones are positioned at spaced apart locations on the mouthguard body; and
one or more interconnective regions of the flexible circuit board substrate configured for enabling electronically coupling of the component zones, wherein a given one of the interconnective regions follows a meandering path having a length greater than the separation between those of the component zones connected by that interconnective region on a direct path along or within the mouthguard body.

One embodiment provides an instrumented mouthguard device wherein the meandering path allows for mounting of the flexible surface board substrate to the mouthguard body independent of sizing irregularities resultant from customization of the mouthguard body to a specific wearer.

One embodiment provides an instrumented mouthguard device wherein the meandering path allows for mounting of the flexible surface board substrate to the mouthguard body such that, for a first component zone, second component zone, and third component zone:
  (i) the component zones are located in:
    a frontal region of the mouthguard body;
    a side region of the mouthguard body; and
    an opposite side region of the mouthguard body from the second component zone; and
  (ii) the frontal region is located on an opposite side of a teeth-receiving channel to the side region and opposite side region.

One embodiment provides an instrumented mouthguard device wherein the frontal region is located on an inner side of the body relative to the protective channel, and the side region and opposite side regions are located on an outer side of the body relative to the protective channel.

One embodiment provides an instrumented mouthguard device wherein a sealing cover is mounted to the body thereby to seal components mounted on both the outer side of the body relative to the protective channel thereby to cover and the inner side of the body relative to the protective channel.

One embodiment provides an instrumented mouthguard device wherein at least one of the interconnective regions has a length that is at least 50% greater than the separation between the connected component zones on a direct path along or within the mouthguard body.

One embodiment provides an instrumented mouthguard device wherein the first and second component zones are located, respectively, in a frontal region and a side region of the mouthguard body.

One embodiment provides an instrumented mouthguard device wherein the first and second component zones are located, respectively, in opposed side regions of the mouthguard body.

One embodiment provides an instrumented mouthguard device including a third component zone, such that component zones are located in:
  a frontal region of the mouthguard body;
  a side region of the mouthguard body; and
  an opposite side region of the mouthguard body from the second component zone;
  wherein the conductive member has a first segment that electronically couples the first and second component zones, and a second segment that electronically couples the second and third component zones.

One embodiment provides an instrumented mouthguard device wherein at least one of the interconnective regions of the flexible circuit board substrate has a length that is at least 50% greater than the separation between the zones it couples on a direct path along or within the mouthguard body.

One embodiment provides an instrumented mouthguard device wherein at each interconnective region of the flexible circuit board substrate has a length that is at least 50% greater than the separation between the zones it couples on a direct path along or within the mouthguard body.

One embodiment provides an instrumented mouthguard device wherein the first component zone is located in the mouthguard body at a frontal region and the second component zone is located in the mouthguard body at a frontal region, and wherein the interconnective region coupling those zones is shaped thereby to provide an expandable region to enable adjustment of overall dentition width thereby to accommodate varying sizes and/or shapes of mouthguard bodies.

One embodiment provides an instrumented mouthguard device wherein the expandable region has slack taken in or proximal a palette region of the mouthguard body.

One embodiment provides an instrumented mouthguard device wherein the first component zone is located in the mouthguard body at a frontal region and the second component zone is located in the mouthguard body at a frontal region, and wherein the conductive member coupling those zones is shaped thereby to provide an expandable region in a cuspid region to enable adjustment of component fit in the mouthguard body.

One embodiment provides an instrumented mouthguard device wherein each of the component zones includes at least one accelerometer device.

One embodiment provides an instrumented mouthguard device wherein at least one of the component zones includes a coupling to a battery module.

One embodiment provides an instrumented mouthguard device wherein at least one of the component zones includes a charging coil.

One embodiment provides an instrumented mouthguard device wherein at least one of the component zones includes a wireless communications module.

One embodiment provides an instrumented mouthguard device wherein at least one of the component zones includes a coupling to an antenna for the wireless communications module.

One embodiment provides an instrumented mouthguard device wherein at least one of the component zones includes a memory module and microprocessor.

One embodiment provides an instrumented mouthguard device wherein at least one of the component zones is formed from a plurality of rigid PCB segments interconnected by flexible regions.

One embodiment provides an instrumented mouthguard device wherein a common substrate in part defines the conductive member and the first and second component zones.

One embodiment provides an instrumented mouthguard device wherein the mouthguard is formed from a process including:
(i) measuring a subject;
(ii) forming an inner mouthguard body member based on the measuring of the subject;
(iii) mounting the component zones and conductive member to an outer face of the inner mouthguard body; and
(iv) sealing an outer mouthguard body member to the inner mouthguard body member thereby to encapsulate the component zones and conductive member.

One embodiment provides an instrumented mouthguard device wherein the step of measuring the subject includes a three-dimensional scanning process.

One embodiment provides an instrumented mouthguard device wherein the inner mouthguard body is formed using a mold generated from the three-dimensional scanning process.

One embodiment provides an instrumented mouthguard device wherein, wherein the component includes:
at least a first and second component zone, wherein the first and second primary component zones are configured to be positioned at spaced apart locations in a mouthguard body; and
a flexible substrate that supports a conductive member electronically coupling the first and second component zones, wherein upon mounting in the mouthguard body the conductive member has a length that is at least 50% greater than the separation between the zones on a direct path along or within the mouthguard body.

One embodiment provides a method of forming a mouthguard device including:
(i) scanning an interior of a subject's mouth;
(ii) forming an inner mouthguard body member based on the scanning of the subject;
(iii) mounting a plurality of component zones and conductive member to an outer face of the inner mouthguard body, wherein the conductive member is irregularly shaped such that it is configured to enable fitting of the component zones at desired locations on inner mouthguard bodies of varied shapes and sizes; and
(iv) sealing an outer mouthguard body member to the inner mouthguard body member thereby to encapsulate the component zones and conductive member.

One embodiment provides a component for an instrumented mouthguard, wherein the component includes:
at least a first and second component zone, wherein the first and second primary component zones are configured to be positioned at spaced apart locations in a mouthguard body; and
a conductive member electronically coupling the first and second component zones, wherein the conductive member is irregularly shaped such that it is configured to enable fitting of the component zones at desired locations on mouthguard bodies of varied shapes and sizes.

Reference throughout this specification to "one embodiment," "some embodiments" or "an embodiment" means that a particular feature, structure or characteristic described in connection with the embodiment is included in at least one embodiment of the present disclosure. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression a device comprising A and B should not be limited to devices consisting only of elements A and B. Any one of the terms "including," or "which includes," or "that includes" as used herein is also an open term that also means including at least the elements/features that follow the term, but not excluding others. Thus, "including" is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the present disclosure will now be described, by way of example only, with reference to the accompanying drawings in which.

DETAILED DESCRIPTION

Figure 1:
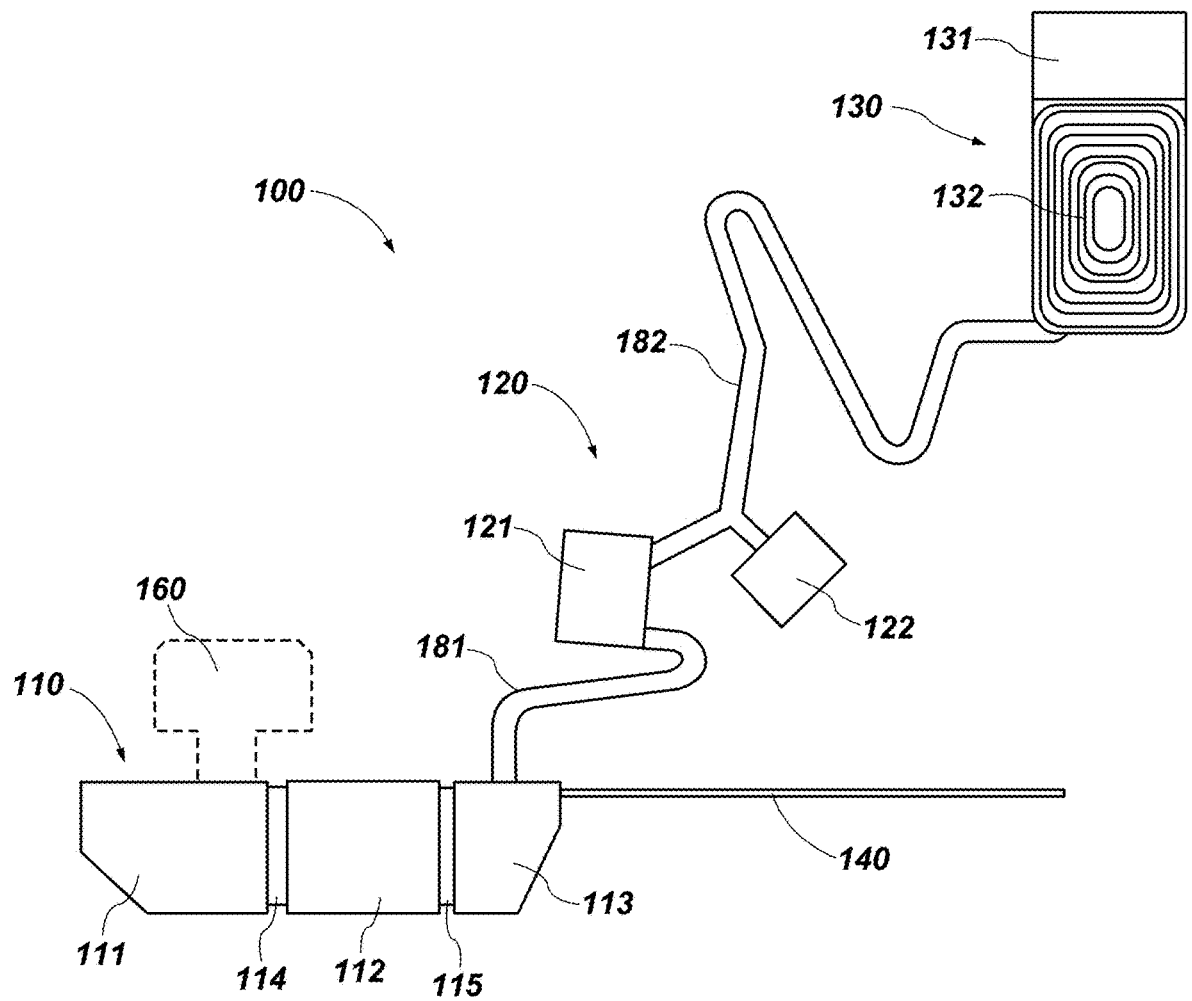
FIG. 1 illustrates a PCB component for an instrumented mouthguard.

Described herein is technology relating to instrumented mouthguard devices, for example, instrumented mouthguards that include components such as accelerometer modules that enable monitoring of head movements of a mouthguard wearer (for example, in the context of collecting date relevant to assessment of brain injuries and the like). Various embodiments that provide instrumented mouthguard devices and components configured for use in instrumented mouthguard devices. In some embodiments, the flexible circuit board substrate is configured to allow sizing irregularities resultant from customization of the mouthguard body to a specific wearer.

In overview, embodiments described below include internal componentry for instrumented mouthguards. It will be appreciated that the shapes and sizes of individuals' mouths and teeth vary significantly across a population (for example, jaw size/shape, teeth size and position, and so on). In this regard, an objective, at least in some cases, is to provide an instrumented unit that is adapted to be fitted into a range of mouthguard bodies having varied shapes and sizes. This allows for a common instrumented unit to be manufactured, and be used with mouthguard bodies that are individually customized for wearers (for example, based on a 3D scanning process). Embodiments described below achieve this goal in a manner that additionally enables the instrumented component to perform well in a flexible mouthguard body, and cope with various impacts and stresses experienced by a mouthguard in use.

Some embodiments provide an instrumented mouthguard device including:
- A mouthguard body that is configured to be worn in a user's mouth—for example, a custom fitted mouthguard body formed using a known user scanning and molding process, or a variation thereof as described below.
- A flexible substrate including at least a first and second component zone, wherein the first and second component zones are positioned at spaced apart locations on the mouthguard body. Preferably, there are three spaced apart component zones—a front zone and two opposite side zones. The component zones each include one or more PCBs.
- Interconnective regions of the flexible substrate for electronically coupling the component zones. This may include a first segment that interconnects a side and front mounted component zone, and a second segment that interconnects the front mounted component zone and opposite side component zone.

In some embodiments, there may be short separations between the component zones and interconnective regions. However, it is preferable in some embodiments that the component zones and interconnective regions are integrally formed by a common substrate. In a preferred example, the conductive member and PCBs are provided on a common flexible substrate; for example, a polyimide substrate that operates as a PCB itself (and has rigid PCB regions mounted thereto and/or formed thereon).

Between at least one pair of the adjacent component zones (and, preferably, between both adjacent pairings side zones and a common frontal zone), the interconnective region has a length that is at least 50% greater than the separation between the zones on a direct path along or within the mouthguard body. In some embodiments, the interconnective region has a length that is at least 100%, 150% or 200% greater than the separation between the component zones on a direct path along or within the mouthguard body. This extended length provides for slack in the conductive member thereby to accommodate varied mouthguard sizes, and provide a robust instrumented device. In preferred embodiments, for at least one segment, the conductive member meanders thereby to provide an "S" shape or partial "S" shape. That is, the segment includes a portion defined by a doubling back of the segment to provide a pair of substantially parallel regions.

Figure 2:
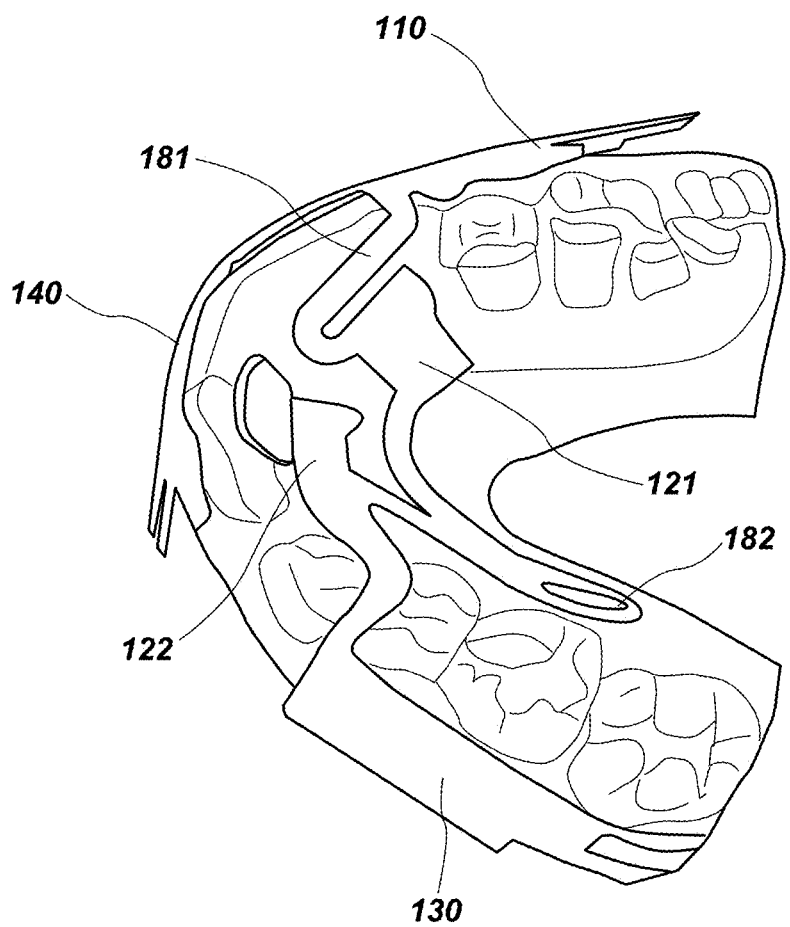
FIG. 2 to FIG. 4 illustrate positioning of the component of FIG. 1 relative to a mouthguard upon construction.
Figure 3:
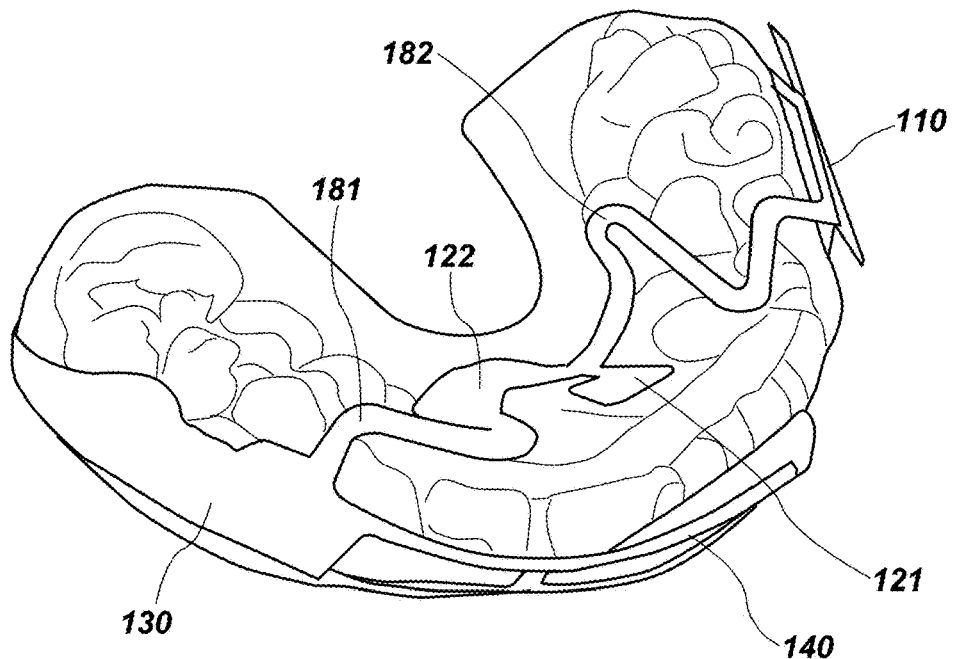
Figure 4:
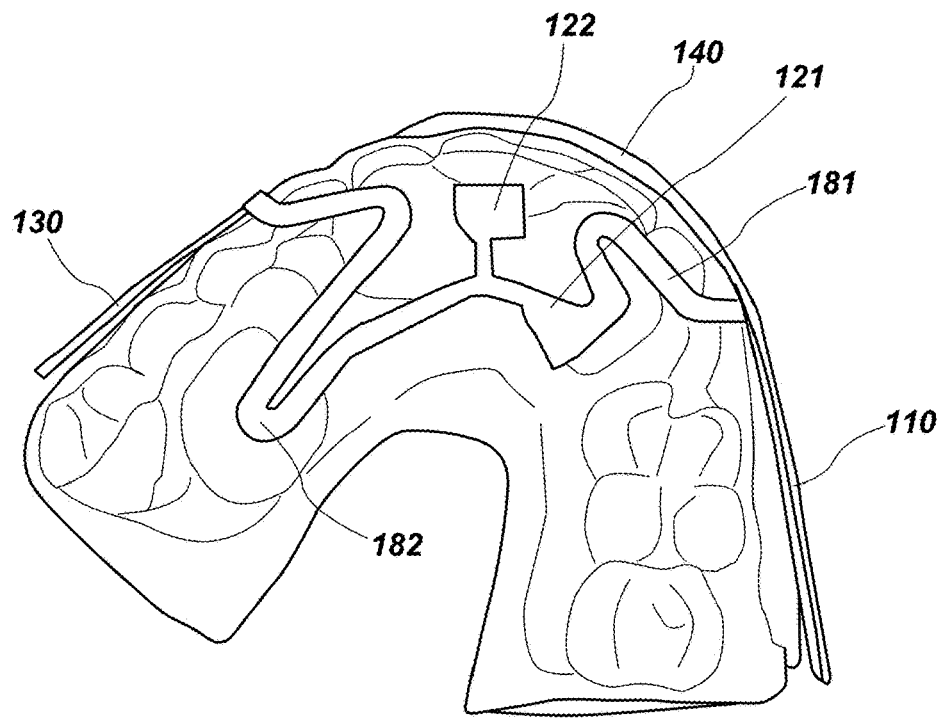

FIG. 1 illustrates an instrumented component 100 according to one embodiment, this being configured for mounting in a mouthguard body thereby to provide an instrumented mouthguard. FIG. 2, FIG. 3 and FIG. 4 show substantially how component 100 is positioned relative to a mouthguard upon instrumented mouthguard construction. As discussed in detail further below, an interconnective region supporting a conductive member electronically couples component zones (e.g., printed circuit board regions), the interconnective region supporting the conductive member being irregularly shaped such that it is configured to enable fitting of the component zones at desired locations on mouthguard bodies of varied shapes and sizes. More particularly, a PCB is formed to meander between component zones in a manner that allows for slack. It will be appreciated that, although a number of zones are discussed, an embodiment of the present disclosure disclosed herein provides an integrally formed PCB substrate that provides a fundamental body for component 100, onto which conductive materials and PCB components are mounted. The PCB substrate may be of variable thickness, and/or have rigidity supports applied, thereby to adjust rigidity on a special basis thereby to protect PCB components as required for robustness.

Component 100 includes three component zones:
- A right side component zone 110. In this example the right side component zone is configured to support PCB components including an accelerometer (3-axis), wireless communications unit, memory and microprocessor.
- A frontal component zone 120. In this example, frontal component zone 120 is split into two separate subzones, with a battery-mounting zone configured to be positioned on the inside of the front teeth, and an accelerometer supporting zone configured to be positioned on the other side of the front teeth (for a 3-axis accelerometer).

A left side component zone 130. In this example the left side component zone provides mounting locations for an accelerometer (3-axis) and battery charging unit.

Flexible connective regions of the substrate connect these zones, including a first segment 181 that electronically couples right side component zone 110 and frontal component zone 120, and a second segment 182 that electronically couples frontal component zone 120 and left side component zone 130. As shown in FIG. 1, segment 181 is over 150% the length of the separation of connection points with zones 110 and 120, and segment 182 is over 200% of the separation of connection points with zones 120 and 130.

The flexible connector member provides a flexible substrate onto which conductive strips and a plurality of PCB components are mounted (for example, PCB components in zones 110, 120 and 130). In some embodiments, the flexible substrate has an increased thickness in certain regions thereby to provide increased rigidity for PCB components that are susceptible to damage as a result of PCB flexion (for example, see regions 111, 112 and 113 discussed below). In some embodiments, additional materials are applied to the flexible substrate thereby to increase rigidity where required.

In the illustrated embodiment, zone 110 is defined by three substantially rigid PCB regions 111, 112 and 113, interconnected by comparatively flexible regions (flex connectors) 114 and 115. This enables a better fit of zone 110 to a curved surface; in the present embodiment, it is configured to be mounted in a right cheek region of the mouthguard body. Zone 110 includes a range of electronic components, including:

A 3-axis accelerometer.

A microprocessor (for example, a QUALCOMM® CSR1012).

A memory module (for example, a Macronix MX25L3233).

A wireless communications module, in this embodiment being a BLUETOOTH® module coupled to a BLUETOOTH® antenna 140, this antenna configured to be mounted such that it runs across a frontal region of the mouthguard forward of a wearer's teeth.

A coupling port to a programming tab 160. Programming tab is shown in dashed lines to indicate that it is removed prior to mounting of component 100 into a mouthguard body.

A Light-Emitting Diode configured to be visible through the mouthguard body, in order to provide a device state indication to a user. For example, this is configured to be positioned behind the wearer's top lip.

It should be appreciated that the variations in rigidity within zone 110 (and across the component generally) is selected based at least in part of PCB components that are to be mounted at the various locations. For example, in one embodiment, one or more of regions 111, 112 and 113 is not rigid, thereby to allow improved curvature upon application to the mouthguard body, and PCB components mounted to the non-rigid region are selected and/or mounted in such a manner to remain robust in spite to flexion in the PCB substrate.

Zone 120 includes a first PCB region 121 to which a battery unit is connected (with the battery being mounted to the mouthguard body in a location that, in use, is positioned behind right hand teeth—for example, battery would be seen to extend from 121 rightwards, covering the second bicuspid and a major portion of two molars based on the constructed example in FIG. 2), and a second PCB region 122 including a 3-axis accelerometer (which is configured to be mounted to the mouthguard body in a location that in use is positioned behind front teeth).

Zone 130 is configured to be mounted on a left cheek region of the mouthguard body, and includes a PCB that carries a 3-axis accelerometer, along with a charging coil to enable wireless charging of the battery unit.

Segment 181 of the conductive member is configured such that, upon mounting to the mouthguard body, it traverses across a bottom region of the mouthguard body at a region adjacent cuspid and first bicuspid (or, alternately, first and second teeth). This allows zone 120 to be provided on an internal region (behind teeth) and zone 110 provided on an external region (in front of teeth).

Segment 182 includes a dentition meander that is configured to position slack primarily on the mouthguard body adjacent inside of the left-hand teeth as much as possible (or alternately, but less preferably, in a palette region proximal the mouthguard body adjacent inside of the left-hand teeth).

Construction of an instrumented mouthguard including component 100 preferably includes:

(i) Measuring a subject. For example, this may include a three-dimensional scanning process that accurately measures the subject's mouth and teeth. The measurement process may alternately include taking a mold.

(ii) Forming an inner mouthguard body member based on the measuring of the subject. This may include forming a mold from the measurement step, and using that to shape resilient mouthguard body materials. In some embodiments, alternate techniques (such as 3D printing) are used.

(iii) Mounting component 100 (i.e., the component zones and conductive member) to an outer face of the inner mouthguard body.

(iv) Sealing an outer mouthguard body member to the inner mouthguard body member thereby to encapsulate component 100.

As further context, a conventional mouthguard manufacture method include vacuum forming one or more (typically two) layers of material over a positive mold of a dentition (for example, a subject's dentition as measured from scanning, molding, or the like). According to an embodiment, a process for manufacturing an instrumented mouthguard is a variation on this. The first layer is vacuum formed to the mold, and then the circuit board defining component 100 is affixed (for example, using adhesive) to the outside of that first layer. A stiff resin or adhesive is used to fill the resulting gaps between the inner layer (which will follow the shape of the teeth) rigid sections of the PCB (which are nominally flat); this supports the circuit board and prevents damage during the next step. That next step is to vacuum form a second layer over the combined first-layer/PCB pair. If the adhesive/resin has been applied correctly, the material should not deform or flex the PCB.

Optional steps include:

Wrapping the circuit board in electro-compatible material, such as polyimide (KAPTON®) tape, to prevent the outer MG layer forming around the individual components and subsequently transferring lateral force to those components, which can damage them.

Encapsulating some or all of the PCB in a semi-rigid epoxy or resin. This performs the same task as the tape, above, but also more strongly adheres the components to the PCB to mitigate the effect of any residual lateral loading and/or flex of the circuit board.

In preferred embodiments, material layers are not modified before vacuum-forming (e.g., to form a recess into which component 100 is positioned); this ensures a minimum thickness of impact-absorbing material throughout the mouthguard (and therefore its function as a mouthguard is not compromised by presence of instrumentation).

In a further embodiment, component 100 or a variant thereof is embedded into a post-manufacture customized (e.g., a "boil and bite") mouthguard. In such an embodiment, a standard generic form is injection molded, and a user heats the mouthguard into a temporarily deformable state and bites firmly into it thereby to shape the resilient materials substantially to their teeth before it cools and becomes stable in the new customized shape.

Figure 5A:
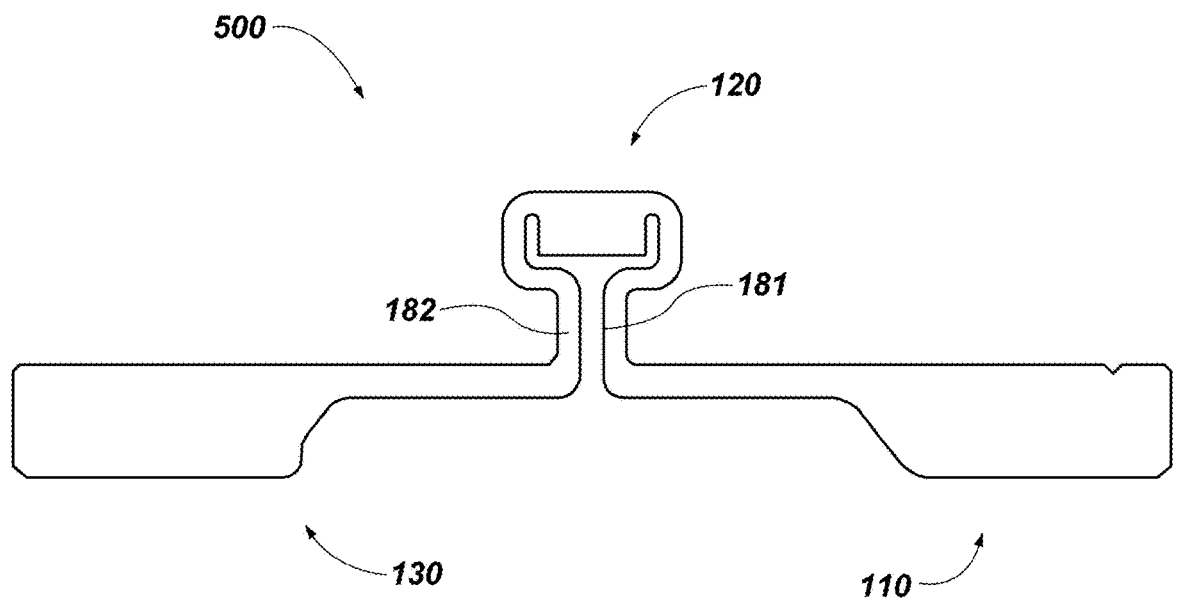
FIG. 5A and FIG. 5B illustrate components for an instrumented mouthguard according to further embodiments.
Figure 5B:
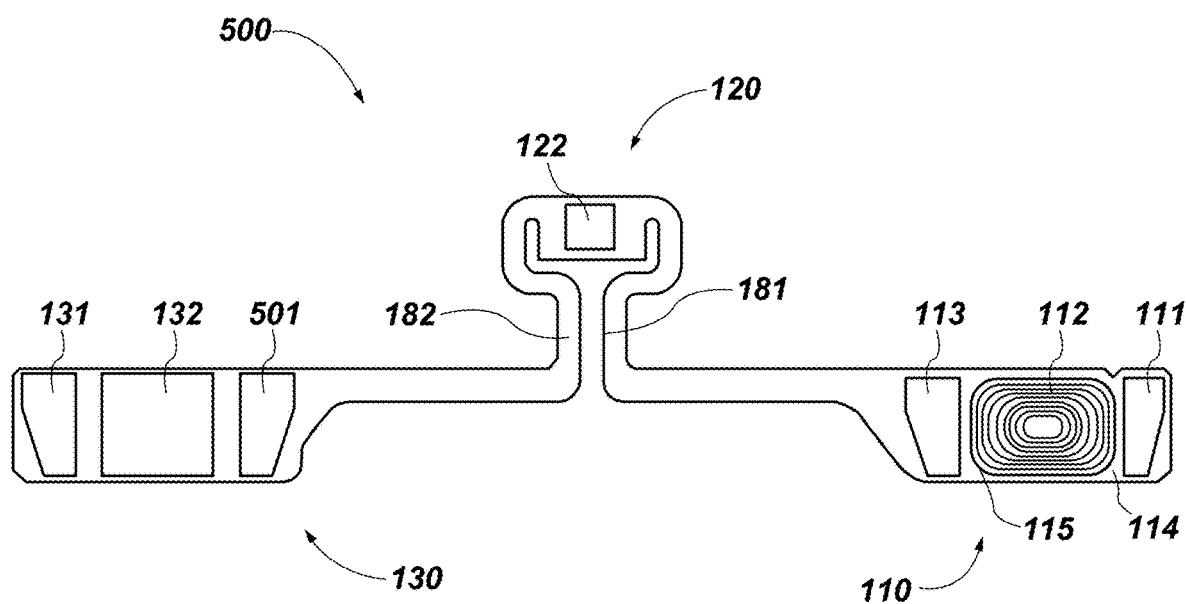
Figure 6A:
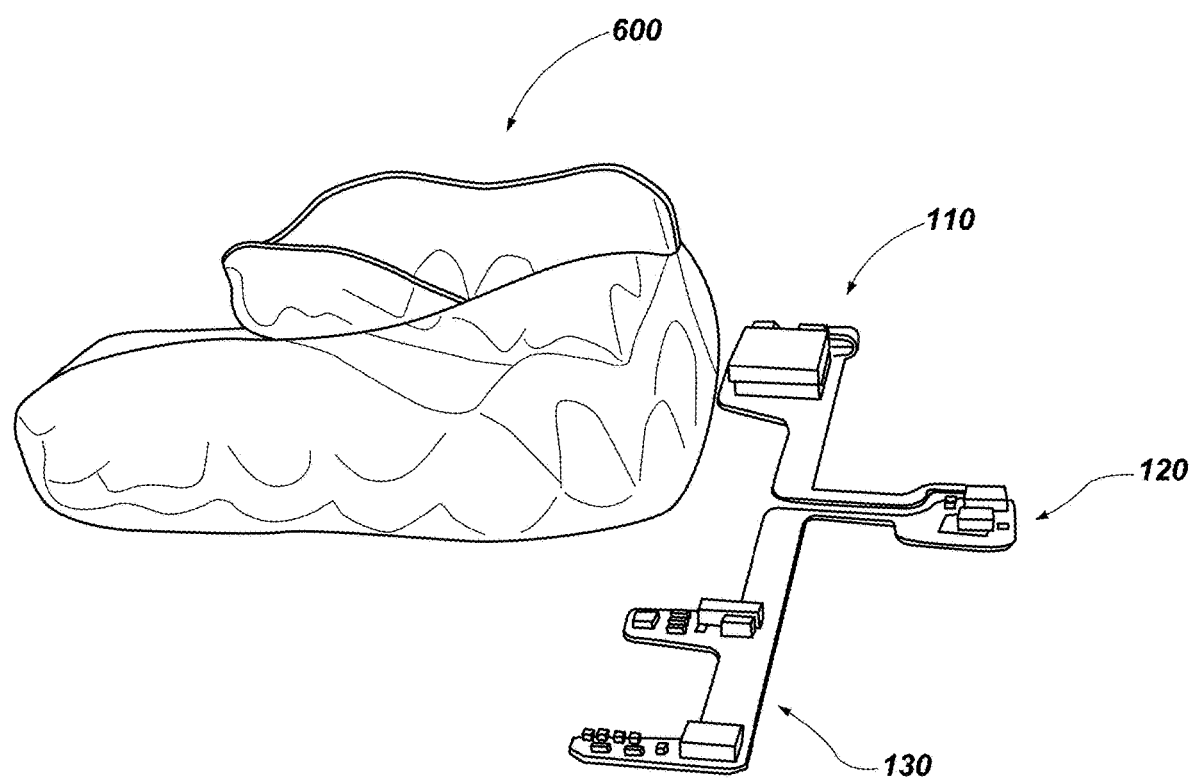
FIG. 6A to FIG. 6D illustrate an instrumented mouthguard according to a further embodiment.
Figure 6B:
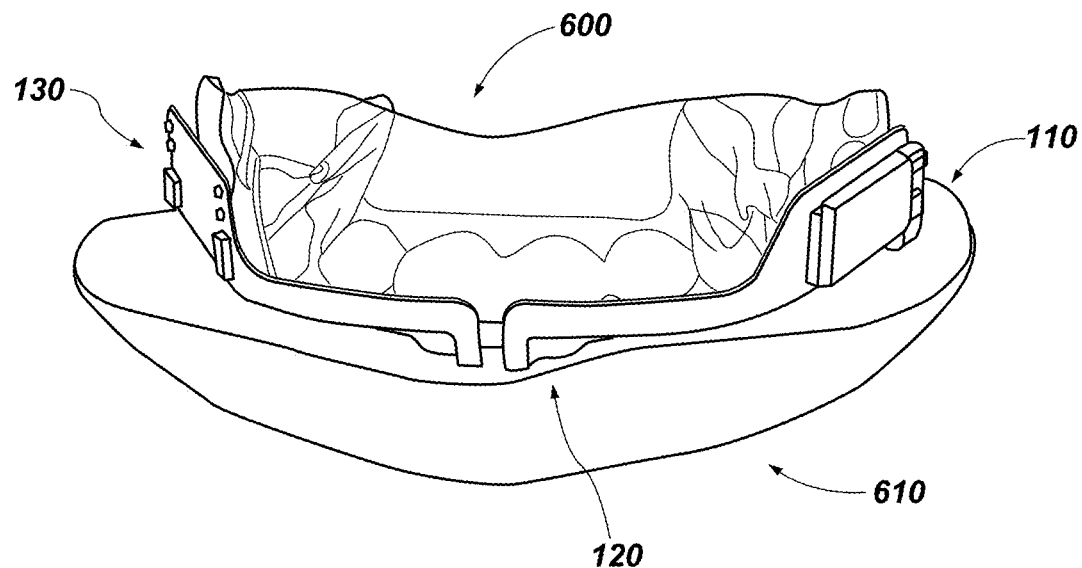
Figure 6C:
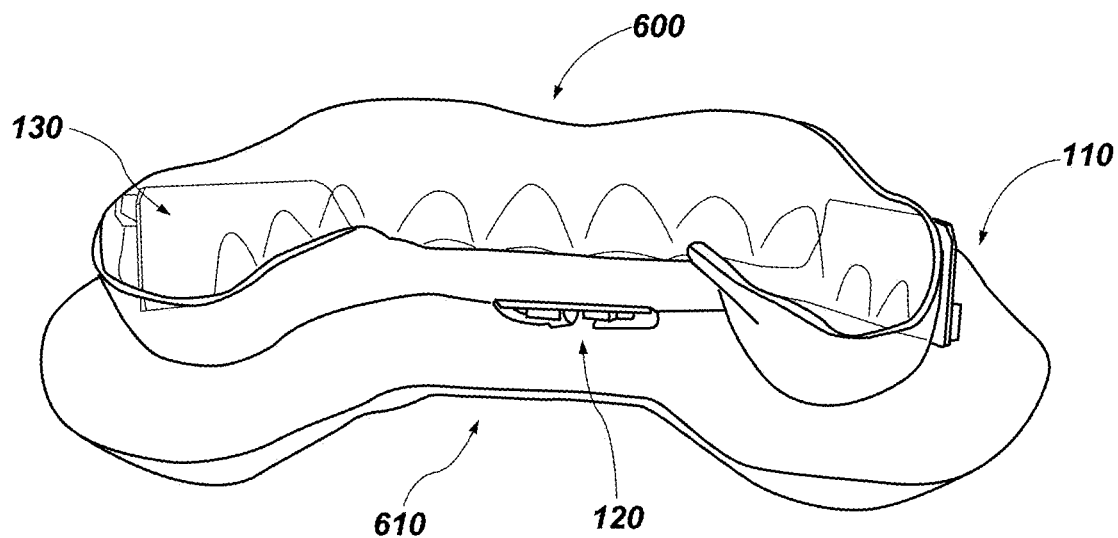
Figure 6D:
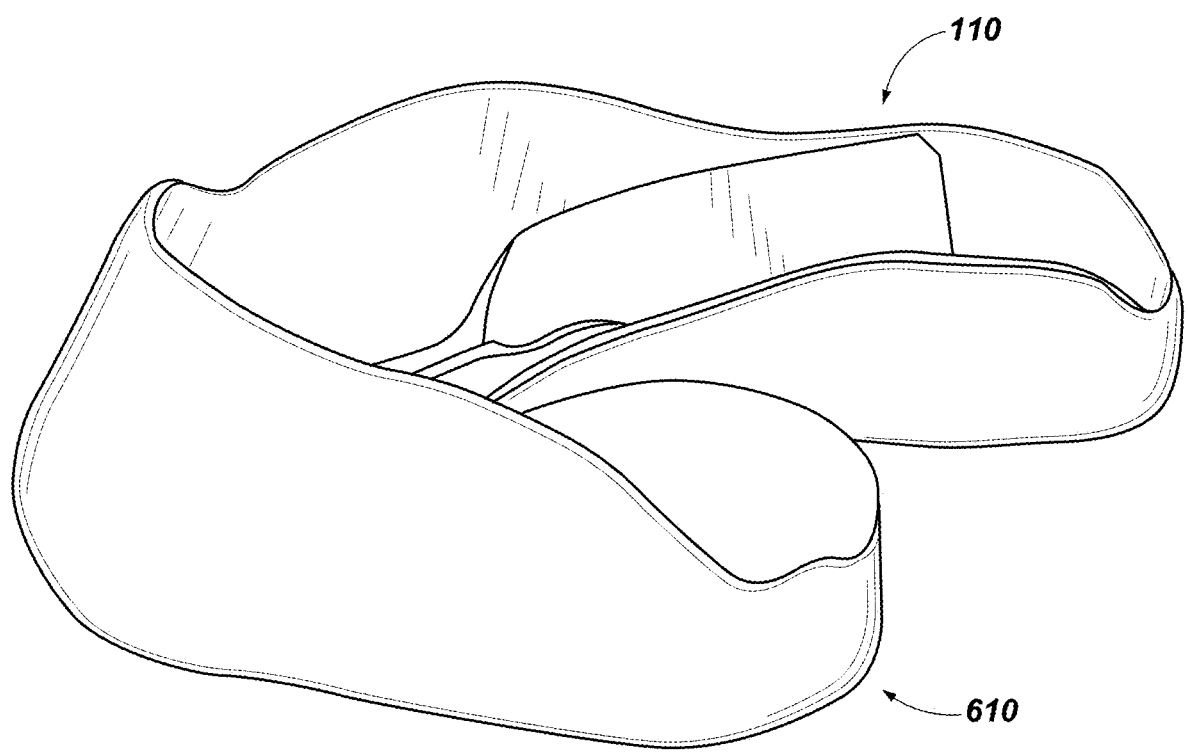

FIG. 5A and FIG. 5B illustrates an instrumented component 500 according to a further embodiment, this being configured for mounting in a mouthguard body thereby to provide an instrumented mouthguard.

As shown in FIG. 5A, component 500 is defined by a flexible circuit board substrate that is configured such that one or more conductive members electronically couples component zones (e.g., printed circuit board regions). The flexible circuit board in this manner defines a conductive member that is irregularly shaped such that it is configured to enable fitting of the component zones at desired locations on mouthguard bodies of varied shapes and sizes. More particularly, a PCB is formed to meander between component zones in a manner that allows for customizable fitting, whilst providing for added flexibility and robustness when the mouthguard is used. This presents a significant advantage over non-meandering PCBs, or the use of wires interconnecting distinct PCBs.

The PCB substrate illustrated in FIG. 5A may be of variable thickness, and/or have rigidity supports applied, thereby to adjust rigidity on a special basis thereby to protect PCB components as required for robustness.

Component 100 includes three component zones:
- A right side component zone 110. In some implementations the right side component zone is configured to support PCB components including an accelerometer (3-axis), wireless communications unit, memory and microprocessor.
- A frontal component zone 120. In some implementations, frontal component zone 120 is split provides an accelerometer supporting zone configured to be positioned on the outer side of the front teeth (for a 3-axis accelerometer).
- A left side component zone 130. In some implementations the left side component zone provides mounting locations for an accelerometer (3-axis), battery charging unit, and a battery mounting location.

The positioning of components described above, and shown in FIG. 5B, is an example only, and in other embodiments, alternate configurations of components are distributed between the component zones.

A flexible connector member, defined by part of the PCB substrate onto which conductors connect these zones, has a first segment 181 that electronically couples right side component zone 110 and frontal component zone 120, and a second segment 182 that electronically couples frontal component zone 120 and left side component zone 130. As shown in FIGS. 5A and 5B, these segments are meandering. In this example, as with examples above, the meandering is such that, segment 181 is over 150% the length of the separation of connection points with zones 110 and 120, and segment 182 is over 200% of the separation of connection points with zones 120 and 130.

The flexible connector member provides a flexible substrate onto which conductive strips and a plurality of PCB components are mounted (for example, PCB components in zones 110, 120 and 130). In some embodiments, the flexible substrate has an increased thickness in certain regions thereby to provide increased rigidity for PCB components that are susceptible to damage as a result of PCB flexion (for example, see regions 111, 112 and 113 discussed below). In some embodiments, additional materials are applied to the flexible substrate thereby to increase rigidity where required.

In the embodiment of FIG. 5B, zone 110 is defined by three substantially rigid PCB regions 111, 112 and 113, interconnected by comparatively flexible regions (flex connectors) 114 and 115. This enables a better fit of zone 110 to a curved surface; in the present embodiment, it is configured to be mounted in a right cheek region of the mouthguard body. Zone 110 includes a range of electronic components, including:
- A 3-axis accelerometer.
- A microprocessor (for example, a QUALCOMM® CSR1012).
- A memory module (for example, a Macronix MX25L3233).
- A wireless communications module, in this embodiment being a BLUETOOTH® module coupled to a BLUETOOTH® antenna (not shown); for example, an antenna configured to be mounted such that it runs across a frontal region of the mouthguard forward of a wearer's teeth.
- A coupling port to a programming tab (not shown).
- A Light-Emitting Diode configured to be visible through the mouthguard body (not shown), in order to provide a device state indication to a user. For example, this is configured to be positioned behind the wearer's top lip.

It should be appreciated that the variations in rigidity within zone 110 (and across the component generally) is selected based at least in part of PCB components that are to be mounted at the various locations. For example, in one embodiment, one or more of regions 111, 112 and 113 is not rigid, thereby to allow improved curvature upon application to the mouthguard body, and PCB components mounted to the non-rigid region are selected and/or mounted in such a manner to remain robust in spite to flexion in the PCB substrate.

Zone 120 includes a second PCB region 122 including a 3-axis accelerometer (which is configured to be mounted to the mouthguard body in a location that in use is positioned behind front teeth).

Zone 130 is configured to be mounted on a left cheek region of the mouthguard body, and includes a PCB that carries a 3-axis accelerometer 131, along with a charging coil 132 to enable wireless charging of a battery unit 151.

In other implementations the battery unit is located in zone 110 or zone 120. In further embodiments, additional components including the likes of gyroscopes may also be present at one or more of the component zones (for example, a gyroscope in combination with an accelerometer at each component zone).

Segment 181 of the conductive member is configured such that, upon mounting to the mouthguard body, it traverses across a bottom region of the mouthguard body at a region approximately adjacent cuspid and first bicuspid (or, alternately, first and second teeth). This allows zone 120 to be provided on an internal region (behind teeth) and zone 110 provided on an external region (in front of teeth). A sealing cover is mounted to the body thereby to seal components mounted on both the outer side of the body relative to the protective channel thereby to cover and the inner side of the body relative to the protective channel.

As shown in FIG. 6A to FIG. 6D, an instrumented mouthguard device is formed from a user-customized body 600, a PCB component having a configuration similar to that shown in FIG. 5A/FIG. 5B, and a sealing cover 610. The meandering path allows for mounting of the flexible surface board substrate to the mouthguard body such that the component zones are located in a frontal region of the mouthguard body (frontal component zone 120); a side region of the mouthguard body (component zone 110); and an opposite side region of the mouthguard body from the second component zone (component zone 130). The frontal region is located on an opposite side of a teeth-receiving channel to the side region and opposite side region. In this example the frontal region is located on an inner side of the body relative to the protective channel, and the side region and opposite side regions are located on an outer side of the body relative to the protective channel. A sealing cover 610 is mounted to the body thereby to seal components mounted on both the outer side of the body relative to the protective channel thereby to cover and the inner side of the body relative to the protective channel.

It should be appreciated that in the above description of exemplary embodiments of the present disclosure, various features of the present disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the claimed invention, and form different embodiments, as would be understood by those skilled in the art. For example, in the following claims, any of the claimed embodiments can be used in any combination.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the present disclosure, those skilled in the art will recognize that other and further modifications may be made thereto without departing from the spirit of the claimed invention, and it is intended to claim all such changes and modifications as falling within the scope of the invention as defined by the claims.

The invention claimed is:

1. An instrumented mouthguard device, comprising:
 a mouthguard body that is configured to be worn in a user's mouth, wherein the body includes a protective channel that is configured to receive and protect the user's upper and/or lower teeth; and
 a flexible circuit board substrate mounted to the mouthguard body, wherein the flexible circuit board substrate includes:
 at least a first and second component zone, wherein the first and second component zones are positioned at spaced apart locations on the protective channel of the mouthguard body; and
 one or more interconnective regions of the flexible circuit board substrate configured for enabling electronically coupling of the component zones, wherein a given one of the interconnective regions follows a meandering path having a length greater than the separation between those of the component zones connected by that interconnective region on a direct path along or within the protective channel of the mouthguard body,
 wherein the meandering path allows for mounting of the flexible circuit board substrate to those regions of the mouthguard body which define the protective channel independent of sizing irregularities resultant from customization of those regions of the mouthguard body which define the protective channel to a specific wearer in a manner which facilitates variations in relative separation and positioning of the first and second component zones on the protective channel of the mouthguard body thereby to account for mouthguard bodies having different shapes and sizes.

2. The mouthguard device of claim 1, wherein the meandering path allows for mounting the first component zone at a first desired location on a mouthguard body that is customized for a specific wearer, and the second component zone at a second desired location on a mouthguard body, wherein the second desired location is selected independent of its positional relationship relative to the first location.

3. The mouthguard device of claim 1, wherein the meandering path allows for mounting of the flexible circuit board substrate to the mouthguard body such that the first component zone is located on an inner side of the body relative to the protective channel which, in use, is disposed between a wearer's teeth and mouth cavity, and the second component zone is located on an outer side of the body relative to the protective channel which is, in use, disposed between the wearer's teeth and lips.

4. The mouthguard device of claim 3, wherein one of the first and second component zones is, in use, adjacent front teeth of the wearer, and the other of the first and second component zones is, in use, adjacent molar teeth of the wearer.

5. The mouthguard device of claim 3, wherein a sealing cover is mounted to the body thereby to seal components mounted on both an outer side of the body relative to the protective channel and an inner side of the body relative to the protective channel.

6. The mouthguard device of claim 1, wherein at least one of the interconnective regions has a length that is at least 50% greater than the separation between the connected component zones on a direct path along or within those regions of the mouthguard body which define the protective channel.

7. The mouthguard device of claim 1, wherein the first and second component zones are located, respectively, in a frontal region and a side region of the mouthguard body.

8. The mouthguard device of claim 1, wherein the first and second component zones are respectively located in opposed side regions of the mouthguard body.

9. The mouthguard device of claim 1, further comprising a third component zone, such that component zones are located in:
- a frontal region of the mouthguard body;
- a side region of the mouthguard body; and
- an opposite side region of the mouthguard body from the second component zone;
- wherein a conductive member has a first segment that electronically couples the first and second component zones, and a second segment that electronically couples the second and third component zones.

10. The mouthguard device of claim 9, wherein at least one of the interconnective regions of the flexible circuit board substrate has a length that is at least 50% greater than the separation between the zones it couples on a direct path along or within those regions of the mouthguard body which define the protective channel.

11. The mouthguard device of claim 9, wherein each interconnective region of the flexible circuit board substrate has a length that is at least 50% greater than the separation between the zones it couples on a direct path along or within those regions of the mouthguard body which define the protective channel.

12. The mouthguard device of claim 1, wherein the first component zone is located in the mouthguard body at a frontal region and the second component zone is located in the mouthguard body at a frontal region, and wherein the interconnective region coupling those zones is shaped thereby to provide an expandable region to enable adjustment of overall dentition width thereby to accommodate varying sizes and/or shapes of mouthguard bodies.

13. The mouthguard device of claim 12, wherein the expandable region has slack taken in or proximal a palette region of the mouthguard body.

14. The mouthguard device of claim 1, wherein the first component zone is located in the mouthguard body at a frontal region and the second component zone is located in the mouthguard body at a frontal region, and wherein the one or more interconnective regions of the flexible circuit board substrate coupling those zones is shaped thereby to provide an expandable region in a cuspid region to enable adjustment of component fit in the mouthguard body.

15. The mouthguard device of claim 1, wherein each of the component zones includes at least one accelerometer device.

16. The mouthguard device of claim 1, wherein at least one of the component zones includes a coupling to a battery module.

17. The mouthguard device of claim 1, wherein at least one of the component zones includes a charging coil.

18. The mouthguard device of claim 1, wherein at least one of the component zones includes a wireless communications module.

19. The mouthguard device of claim 1, wherein at least one of the component zones includes a coupling to an antenna for a wireless communications module.

20. The mouthguard device of claim 1, wherein at least one of the component zones includes a memory module and microprocessor.

21. The mouthguard device of claim 1, wherein at least one of the component zones is formed from a plurality of rigid PCB segments interconnected by flexible regions.

22. The mouthguard device of claim 1, wherein a common substrate in part defines the one or more interconnective regions of the flexible circuit board substrate and the first and second component zones.

23. The mouthguard device of claim 1, wherein the mouthguard is formed from a process including:
   (i) measuring a subject;
   (ii) forming an inner mouthguard body member based on the measuring of the subject;
   (iii) mounting the component zones and the one or more interconnective regions of the flexible circuit board substrate to an outer face of the inner mouthguard body, in a manner which facilitates variations in relative separation and positioning of the component zones on the protective channel of the mouthguard body thereby to account for mouthguard bodies having different shapes and sizes; and
   (iv) sealing an outer mouthguard body member to the inner mouthguard body member thereby to encapsulate the component zones and the one or more interconnective regions of the flexible circuit board substrate.

24. The mouthguard device of claim 23, wherein the step of measuring the subject includes a three-dimensional scanning process.

25. The mouthguard device of claim 24, wherein the inner mouthguard body is formed using a mould generated from the three-dimensional scanning process.

26. A method of forming a mouthguard device, comprising:
   (i) scanning an interior of a subject's mouth;
   (ii) forming an inner mouthguard body member based on the scanning of the subject, such that the shape and size of the inner mouthguard body member is customized for the user based on the scanning;
   (iii) mounting a plurality of component zones and a conductive member to an outer face of a protective channel provided by the inner mouthguard body in a manner which facilitates variations in relative separation and positioning of the component zones on the protective channel of the mouthguard body thereby to account for the customized shape and size of the inner mouthguard body, wherein the protective channel surrounds and protects a wearer's teeth and the conductive member is irregularly shaped such that it is configured to enable fitting of the component zones at desired locations on inner mouthguard bodies of varied shapes and sizes; and
   (iv) sealing an outer mouthguard body member to the inner mouthguard body member thereby to encapsulate the component zones and conductive member.

* * * * *